(12) United States Patent
Bernhard et al.

(10) Patent No.: US 8,235,886 B2
(45) Date of Patent: Aug. 7, 2012

(54) IMPLANTABLE FIXATION ASSEMBLY FOR REMOVABLY SECURING MEDICAL DEVICE

(75) Inventors: Hans Bernhard, Köniz (CH); Markus Haller, Yens (CH); Patrizio Visino, Areuses (CH)

(73) Assignee: Advanced Bionics AG, Zug (CH)

( * ) Notice: Subject to any disclaimer, the term of this patent is extended or adjusted under 35 U.S.C. 154(b) by 730 days.

(21) Appl. No.: 11/719,689

(22) PCT Filed: Nov. 30, 2005

(86) PCT No.: PCT/AU2005/001800
§ 371 (c)(1),
(2), (4) Date: Mar. 20, 2008

(87) PCT Pub. No.: WO2006/058367
PCT Pub. Date: Jun. 8, 2006

(65) Prior Publication Data
US 2008/0300596 A1 Dec. 4, 2008

Related U.S. Application Data

(60) Provisional application No. 60/631,508, filed on Nov. 30, 2004, provisional application No. 60/631,512, filed on Nov. 30, 2004.

(51) Int. Cl.
*H04R 25/00* (2006.01)
(52) U.S. Cl. ............ 600/25; 606/300; 606/60; 606/277; 606/324; 606/151; 607/55; 607/56; 607/57; 381/322; 381/324; 411/133; 411/140; 411/321; 411/948

(58) Field of Classification Search ............... 606/54, 606/60, 74, 75, 145, 150, 300, 57, 58; 411/133, 411/140, 321, 948; 600/25; 607/55–57; 381/322, 324
See application file for complete search history.

(56) References Cited

U.S. PATENT DOCUMENTS
2,355,901 A * 8/1944 Beede ............... 411/320
(Continued)

FOREIGN PATENT DOCUMENTS
FR 2633345 A 12/1989
SU 952244 A 8/1982

OTHER PUBLICATIONS
International Search Report. PCT/AU2005/001800. Jan. 13, 2006.

*Primary Examiner* — Kevin T Truong
*Assistant Examiner* — Samuel Hanna
(74) *Attorney, Agent, or Firm* — Roberts Mlotkowski Safran & Cole, P.C.; David S. Safran

(57) ABSTRACT

An implantable fixation assembly (30) for removably securing a (medical) device in a human body is disclosed. The assembly includes: an anchor portion (1) securable to bone; a pair of spaced apart legs (15), at least one leg (15) being resiliently flexible, the ends (15a) of the legs (15) attached to the anchor portion (1); a clamp portion (2) attached towards or at the ends (15a) of the legs (15); a screw and nut combination having an axis of rotation longitudinal to the legs, the combination operably engaging at least one of the legs (15) so as to pull them together or push them apart thereby actuating the clamp portion (2) to secure the device, wherein the actuating is reversible for selectively gripping and releasing the device.

12 Claims, 5 Drawing Sheets

U.S. PATENT DOCUMENTS

| | | | |
|---|---|---|---|
| 3,164,114 A * | 1/1965 | Whitman et al. | 269/52 |
| 4,478,546 A * | 10/1984 | Mercer | 411/385 |
| 4,896,663 A * | 1/1990 | Vandewalls | 606/79 |
| 5,788,711 A * | 8/1998 | Lehner et al. | 606/130 |
| D433,928 S * | 11/2000 | Alcone | D8/382 |
| 6,390,970 B1 * | 5/2002 | Muller | 600/25 |
| 6,537,199 B1 * | 3/2003 | Muller et al. | 600/25 |
| 6,705,985 B2 | 3/2004 | Easter et al. | |
| 2002/0038072 A1 * | 3/2002 | Muller et al. | 600/25 |
| 2007/0249890 A1 * | 10/2007 | Muller et al. | 600/25 |

* cited by examiner

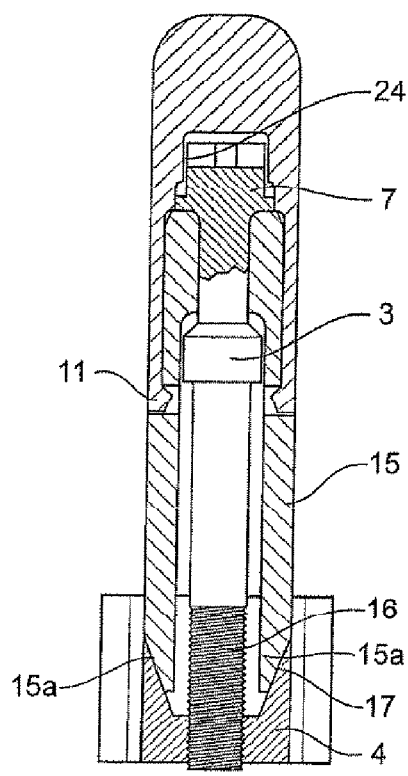
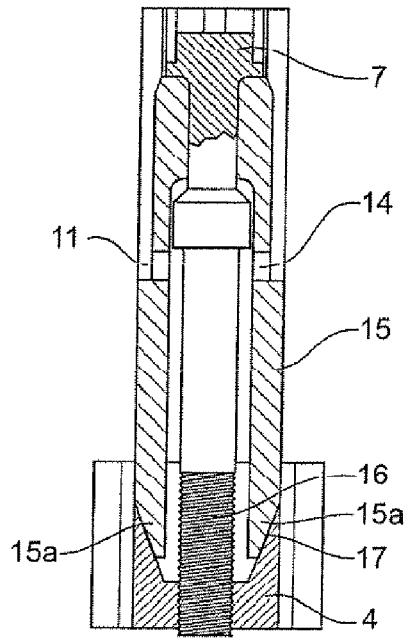
Fig 5a  Fig 5b
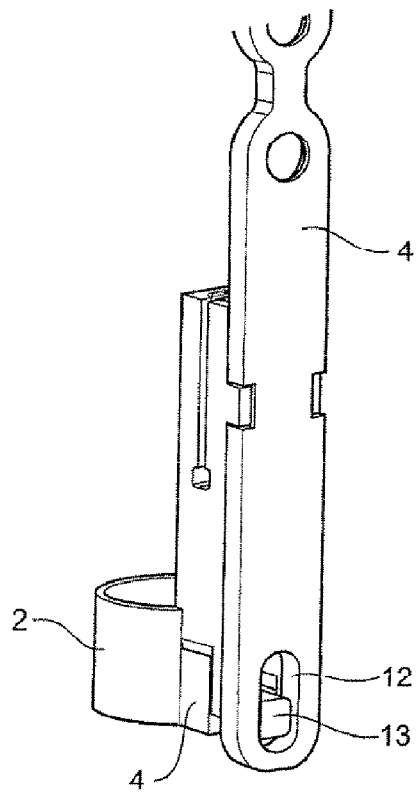
Fig 6

IMPLANTABLE FIXATION ASSEMBLY FOR REMOVABLY SECURING MEDICAL DEVICE

CROSS REFERENCE TO RELATED APPLICATIONS

This application is a national stage application under 35 USC §371(c) of PCT Application No. PCT/AU2005/001800, entitled "Implantable Fixation Assembly For Removably Securing A Medical Device," filed on Nov. 30, 2005, which claims the priority of U.S. Provisional Patent No. 60/631,508 entitled, "Implantable Fixation System For Anchorage Of A Medical Device," filed on Nov. 30, 2004, and claims the priority of U.S. Provisional Patent No. 60/631,512 entitled, "Implantable Actuator For Hearing Aid Applications," filed on Nov. 30, 2004. The entire disclosure and contents of the above applications are hereby incorporated by reference herein.

FIELD OF THE INVENTION

The present invention relates to the fixation of implantable medical devices within or onto a human.

BACKGROUND OF INVENTION

A continuing trend in the health care industry is the increasing quantity of devices permanently or temporarily implanted in the human body for therapeutic and monitoring purposes. To be able to optimally perform their functions, such implantable medical devices have to be placed in a proper location and remain in that location for the duration of the treatment. Thus there is a growing need for reliable anchoring assemblies that are simple to apply with standard surgical instruments and that provide enough flexibility to cover most of the individual patient anatomies. It may be desirable to remove and/or exchange the implanted medical device with a replacement device in the same location when, for example, the original medical device malfunctions.

SUMMARY OF THE INVENTION

According to a first aspect of the invention there is provided an implantable fixation assembly for removably securing a medical device in a human body, the assembly comprising:
  an anchor portion securable to bone;
  a body attached to the anchor portion, the body having a pair of spaced apart legs, at least one leg being flexible, each leg having a distal end;
  a clamp portion attached towards or at the distal ends of the legs;
  a clamp actuating mechanism comprising a driving member that abuts the legs so as to produce a wedging action that induces a lateral force that pulls the legs together or pushes the legs apart as the driving member is driven longitudinally with respect to the legs thereby actuating the clamp portion to secure the device,
  wherein the actuating is reversible for selectively gripping and releasing the device.

Preferably at least one flexible leg is resiliently flexible.

Preferably the clamp portion comprises a part-cylindrical band, the band having an internal diameter that reduces as the clamp is actuated to grip the device.

Preferably the band has a first end attached towards or at the distal ends of a first of the legs and a second end attached towards or at the distal ends of a second of the legs.

Preferably the screw has a head, the head shaped to receive a driver, whereby a surgeon can selectively grip and release the device using the driver.

Preferably the assembly further comprises a safety catch, the catch operable to reversibly lock the clamp with respect to the device.

Preferably the head defines a plurality of longitudinally extending slits for receiving a screw locking portion of the safety catch.

Preferably the catch comprises a screw locking portion selectively engagable with the slits of the screw head.

Preferably the catch further comprises flexible fingers, each finger having a retention portion that snaps into a recess within the legs or the body so as to reversibly secure the safety catch to the legs or body.

Preferably the anchor portion defines a plurality of holes, the holes facilitating attachment of the anchor portion to the bone with screws.

Preferably the anchor portion is bendable to allow a surgeon to conform the anchor portion to a particular anatomy of a patient.

Preferably the assembly further comprises the device, the device having a grippable outer surface, the device and the clamp mutually shaped to allow sliding and rotational movement of the device with respect to the clamp,
  wherein a surgeon can adjust the position of the device with respect to the clamp before releaseably locking the device to the clamp.

According to a second aspect of the invention there is provided an implantable fixation assembly for removably securing a medical device in a human body, the assembly comprising:
  an anchor portion securable to bone;
  a pair of spaced apart legs, at least one leg being flexible, each leg having a proximal end and a distal end, the proximal ends attached to the anchor portion;
  a clamp portion attached towards or at the distal ends of the legs;
  a screw and nut combination having an axis of rotation longitudinal to the legs, the combination operably engaging at least one of the legs so as to pull them together or push them apart thereby actuating the clamp portion to secure the device,
  wherein the actuating is reversible for selectively gripping and releasing the device.

Preferably at least one flexible leg is resiliently flexible.

Preferably the clamp portion comprises a part-cylindrical band, the band having an internal diameter that reduces as the clamp is actuated to grip the device.

Preferably the band has a first end attached towards or at the distal ends of a first of the legs and a second end attached towards or at the distal ends of a second of the legs.

Preferably the nut abuts the legs at a plane that is inclined with respect to a plane orthogonal to the axis of rotation,
  thereby producing a wedging action that induces a lateral force as the nut is driven longitudinally with respect to the legs.

Preferably the screw has a head, the head shaped to receive a driver, whereby a surgeon can selectively grip and release the device using the driver.

Preferably the assembly further comprises a safety catch, the catch operable to reversibly lock the clamp with respect to the device.

Preferably the head defines a plurality of longitudinally extending slits for receiving a screw locking portion of the safety catch.

Preferably the safety catch comprises a screw locking portion selectively engagable with the slits of the screw head.

Preferably the catch further comprises flexible fingers, each finger having a retention portion that snaps into a recess within the legs or the body so as to reversibly secure the safety catch to the legs or body.

Preferably the anchor portion defines a plurality of holes, the holes facilitating attachment of the anchor portion to the bone with screws.

Preferably the anchor portion is bendable to allow a surgeon to conform the anchor portion to a particular anatomy of a patient.

Preferably movement of the nut is restricted so as to prevent the nut from separating from the screw.

Preferably the nut has a projection, the projection constrained to move within a slot defined by any of the body, the arm or the anchor portion.

Preferably the nut is cup shaped with an inner surface that engages the distal ends of the legs.

Preferably the assembly further comprise the device, the device having a grippable outer surface the device and the clamp mutually shaped to allow sliding and rotational movement of the device with respect to the clamp,
wherein a surgeon can adjust the position of the device with respect to the clamp before releaseably locking the device to the clamp.

According to a third aspect of the invention there is provided an implantable fixation assembly for removably securing a medical device in a human body, the assembly comprising:
an anchor portion securable to bone;
a body attached to the anchor portion, the body having a pair of spaced apart legs, at least one leg being flexible, each leg having a distal end;
a clamp portion attached towards or at the distal ends of the legs;
a threaded member, the threaded member threaded to the body and having a shaft extending longitudinally with respect to the legs, the shaft having a head at a proximal end and an enlarged portion at or adjacent a distal end, the enlarged portion operably engaging at least one of the legs so as to pull the legs together or push the legs apart as the threaded member is rotated thereby actuating the clamp portion to secure the device,
wherein the actuating is reversible for selectively gripping and releasing the device.

Preferably the at least one flexible leg is resiliently flexible.

Preferably the clamp portion comprises a part-cylindrical band, the band having an internal diameter that reduces as the clamp is actuated to grip the device.

Preferably the band has a first end attached towards or at the distal ends of a first of the legs and a second end attached towards or at the distal ends of a second of the legs.

Preferably the screw has a head, the head shaped to receive a driver, whereby a surgeon can selectively grip and release the device using the driver.

Preferably the assembly further comprises a safety catch, the catch operable to reversibly lock the clamp with respect to the device.

Preferably the head defines a plurality of longitudinally extending slits for receiving a screw locking portion of the safety catch.

Preferably the catch comprises a screw locking portion selectively engagable with the slits of the screw head.

Preferably the catch further comprises flexible fingers, each finger having a retention portion that snaps into a recess within the legs or the body so as to reversibly secure the safety catch to the legs or body.

Preferably the anchor portion defines a plurality of holes, the holes facilitating attachment of the anchor portion to the bone with screws.

Preferably the anchor portion is bendable to allow a surgeon to conform the anchor portion to a particular anatomy of a patient.

Preferably the assembly further comprises the device, the device having a grippable outer surface, the device and the clamp mutually shaped to allow sliding and rotational movement of the device with respect to the clamp,
wherein a surgeon can adjust the position of the device with respect to the clamp before releaseably locking the device to the clamp.

According to a fourth aspect of the invention there is provided an implantable fixation assembly for removably securing a medical device in a human body, the assembly comprising:
a reversible clamping mechanism having a clamp portion and a screw pulling up a nut which tightens the clamp portion by transforming longitudinal forces into lateral forces through an inclined plane.

Specific embodiments of the invention will now be described in some further detail with reference to and as illustrated in the accompanying figures. These embodiments are illustrative, and are not meant to be restrictive of the scope of the invention.

BRIEF DESCRIPTION OF THE DRAWINGS

Preferred embodiments of the invention are illustrated in the accompanying representations in which:

FIGS. 5a and 5b are cross-sectional views of the clamping and locking mechanism shown in the above Figures, taken along a planes through an axis of the screw;

FIG. 6 is a detailed perspective view of one embodiment of the nut mounted in the clamping mechanism shown in the above Figures;

DETAILED DESCRIPTION OF PREFERRED EMBODIMENTS OF THE INVENTION

Embodiments of the present invention illustrated in the Figures are generally directed to an implantable fixation assembly for securing an implanted device such as a medical device in a patient. Implantable medical devices may include sensors, actuators and the like. Certain embodiments of the present invention comprise a bone plate having one or more extensions each having one or more holes to screw or otherwise attach the extension to an adjacent bone. The implantable fixation assembly also includes a lockable reversible clamping mechanism operable to detachably secure the medical device to the bone plate, thereby reversibly attaching the medical device to a desired bony structure in the patient's body.

Advantageously, embodiments of the implantable fixation assembly of the present invention provide a surgeon with the capability to place a medical device at any desired location in a patient's body without having to make an incision much larger than the medical device and to easily access the clamping mechanism which may be activated near the body surface.

Advantageously, the clamping mechanism is reversible; that is, it detachably secures the medical device to the patient. As such, a medical device that may need to be replaced, for example, due to an upgrade, recall, damage or other reason, can simply be exchanged by detaching the implanted medical device and securing the replacement medical device, while keeping the fixation assembly in place.

Figure 1:
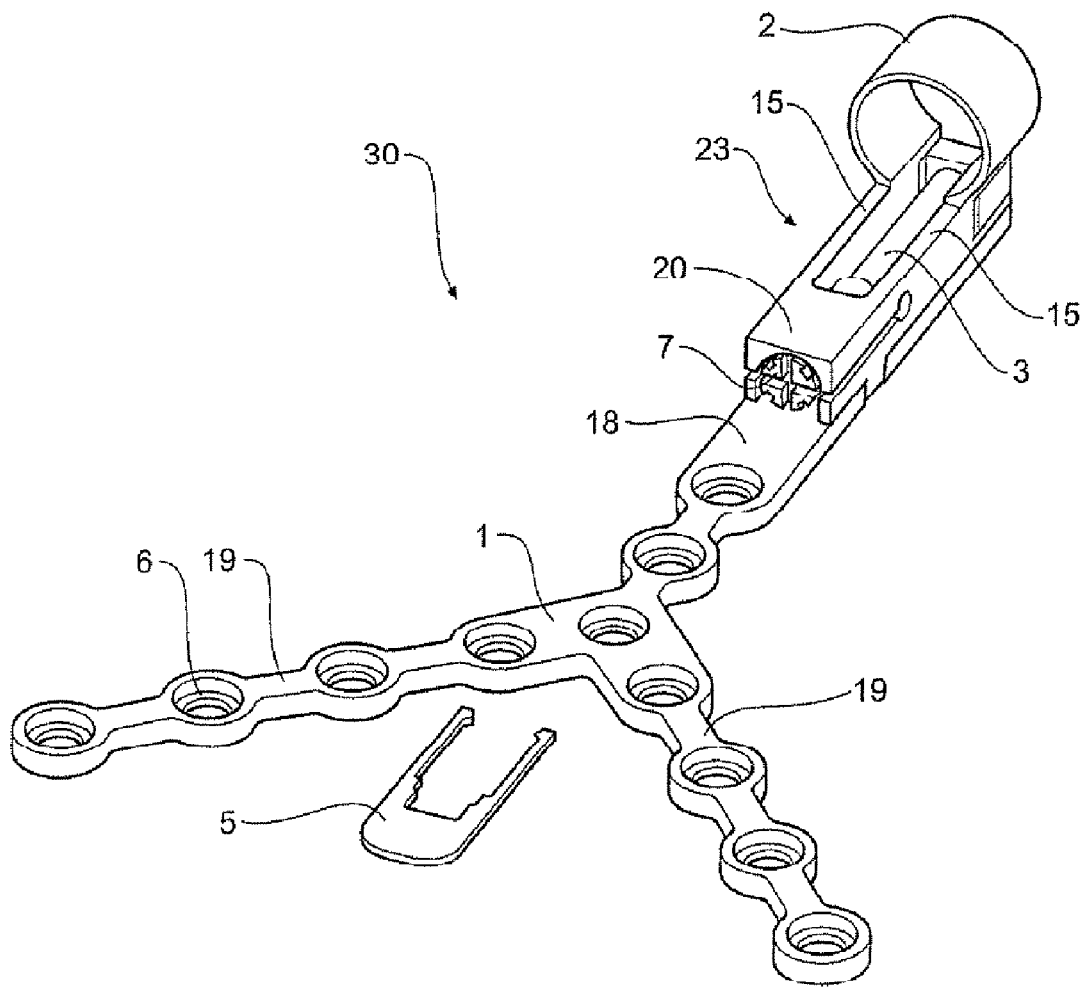
FIG. 1 is a perspective view of a first embodiment of an implantable fixation assembly according to the present invention.

Referring to FIG. 1 an implantable fixation assembly 30 for removably securing a device in or on a human body is shown. The assembly 30 includes an anchor portion 1 in the form of a bone plate that is securable to a bone, a body 20 attached to the anchor portion 1 and a clamp portion 2. The body 20 has a pair of spaced apart legs 15 which are more clearly shown in FIG. 5. The legs 15 are flexible and each has a distal end 15a. The clamp portion 2 is attached to the distal ends 15a of the legs 15.

A clamp actuating mechanism including a driving member in the form of a nut 4 is shown most clearly in FIG. 5. The nut abuts the distal ends 15a of the legs at a plane that is inclined so as to produce a wedging action that induces a lateral force that pushes the legs together as the nut is driven longitudinally with respect to the legs 15. The nut 4 is driven longitudinally by the action of the screw 3 having a thread 16.

Bone plate 1 is configured to attach the fixation assembly to one or more selected bones of the patient. Bone plate 1 has one or more extensions 19 configured to attach directly to a bone of the patient. Each extension 19 comprises one or more screw holes 6 which provide a degree of freedom to choose the number and the location of bone screws (not shown) according to the individual needs. As one of ordinary skill in the art would appreciate, the dimensions of screw holes 6 are suitable for the dimensions of the selected screw which, in turn, is dependent upon a variety of factors including, but not limited to, the size of the bone, the functions performed by the medical device, the mass of the medical device, etc.

Preferably, one or more of the extensions 19 can be modified such as by bending, shortening, etc., by a surgeon in order to be adapted to the individual anatomy of the patient. Alternatively, bone plate 1 can be manufactured with a quantity of extensions 19 each having dimensions suitable for a particular application.

Bone plate 1 further comprises an arm portion 18 that joins extensions 19. In the embodiment shown in FIGS. 1 and 2, arm portion 18 and extensions 19 are portions of a unitary bone plate 1. In alternative embodiments, however, arm portion 18 may be separately manufactured and attached to one or more extensions 19 to form bone plate 1. Arm portion 18 is configured to support a clamping mechanism 23 for detachably securing a medical device to bone plate 1. Clamping mechanism 23 is described in detail below.

Figure 2:
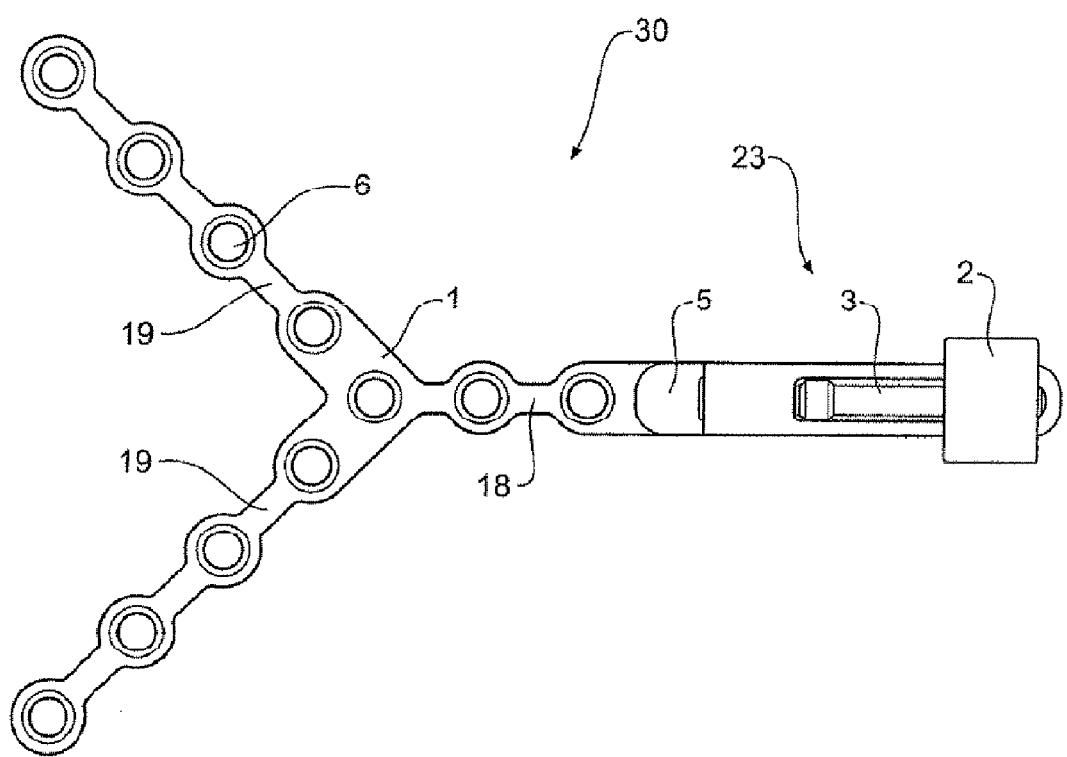
FIG. 2 is a top view of the assembly shown in FIG. 1.

In the embodiment shown in FIGS. 1 and 2, arm portion 18 also has screw holes 6 to attach a portion of arm portion 18 to a bone. It should be appreciated, however, that in alternative embodiments arm portion 18 does not have any screw holes 6.

In the embodiment shown in FIGS. 1 and 2, arm portion 18 is straight, although it need not be straight in all embodiments. In one embodiment, arm portion 18 can be bent by, for example, tip to 90°, in order to place clamp 2 in its final desired location to receive a medical device.

Figure 3:
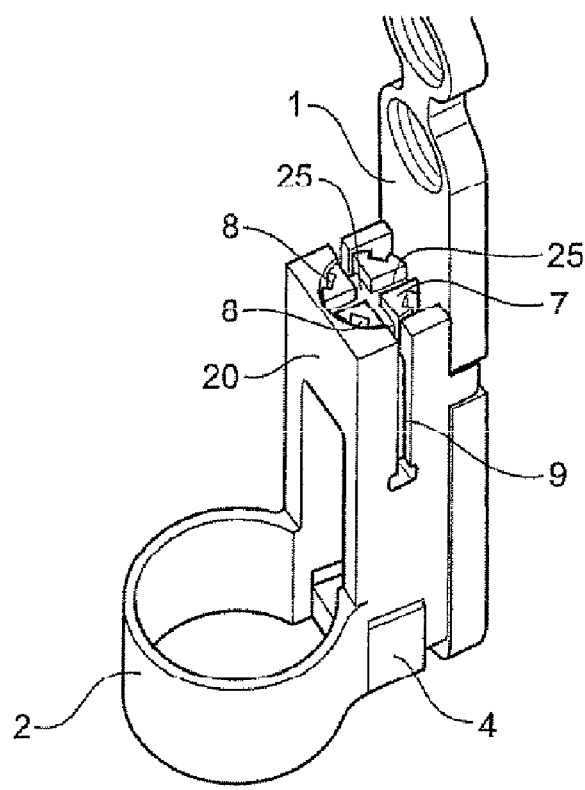
FIG. 3 is a detailed view of a portion of the assembly shown in FIG. 1.
Figure 4:
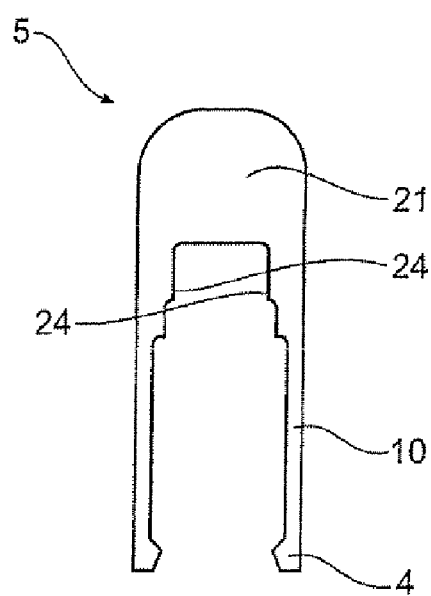
FIG. 4 is a detailed view of one embodiment of a safety catch utilized in embodiments of the anchoring system of the present invention.

The clamping and locking features of clamping mechanism 23 will now be described with reference to FIGS. 1-6. FIGS. 1-2 have been introduced above. FIG. 3 is a perspective view of one embodiment of clamping mechanism 23 of the anchoring assembly shown in FIG. 1. FIG. 4 is a perspective view of one embodiment of a safety catch 5 which is configured to be inserted in clamping mechanism 23 to clampingly secure the inserted medical device. FIG. 5 is a cross-sectional view of the clamping mechanism 23 taken along a plane through an axis of screw 3 in FIG. 1. FIG. 6 is a detailed view of one embodiment of nut 4 mounted in clamping mechanism 23.

Referring to FIGS. 1-6, clamping mechanism 23 comprises a clamp portion 2 formed, in this embodiment, by a thin part-cylindrical band that has the same internal shape as the exterior surface of the medical device which is to be anchored to the patient. In the embodiment shown in FIG. 3, the shape of clamp portion 2 is cylindrical to provide a rotational degree of freedom for a medical device having a cylindrical exterior housing. As one of ordinary skill in the art would appreciate, the cross-sectional shape of the clamping portion 2 of clamp mechanism 23 may be other than circular. For example, in alternative embodiments, clamp portion 2 has a non-symmetric cross-sectional shape such as an oval or square to prevent rotation of the installed medical device.

To anchor a medical device to the bone, the medical device is simply slid into clamp portion 2 until a desired insertion depth is attained. Then, the medical device is secured to clamping mechanism 23 by fastening screw 3. In the illustrative embodiment, screw 3 has a screw head 7 comprising multiple slits 8. Screw head 7 has, in this embodiment, conventional slots 25 to operably receive a screwdriver head of a surgical instrument (not shown).

With the embodiment described above, the screw is a screw drivable by a conventional screwdriver. Other embodiments of the invention may include a screw or bolt having an alien key head or any other drivable head. It should be understood that, in the context of this application and its claims, the term "screw" encompasses bolts and other cylindrical members with a helical ridge type thread.

As best shown in FIG. 5, screw 3 is engaged with nut 4. As screw 3 is rotated clockwise, it draws nut 4 towards screw head 7. To prevent nut 4 from being removed by unfastening screw 3, its movement is limited by projection 13 that travels in a channel 12 in bone plate 1. Through the inclined plane 17 between the cup shaped inner surface 4a of nut 4 and legs 15 of clamping mechanism 23, the longitudinal force is transformed into a lateral force that tightens clamp 2.

To prevent screw 3 from rotating, slits 8 of screw head 7 are to be aligned with opposing grooves 9 in clamp mechanism 23, and safety catch 5 is inserted into clamping mechanism 23, as shown in FIG. 1. As best shown in FIGS. 1 and 4, this embodiment of safety catch 5 comprises a tab 21 with two opposing flexible legs 10 each with a small retention portion 11 located at their distal ends.

When safety catch 5 is inserted into groove 9 of clamping mechanism 2, arms 10 are positioned in slits 8 of screw head 7 and grooves 9 of clamping mechanism 2. Also, a screw locking portion 24 of tab 21 is positioned within slits 8 of screw head 7. Thus, the insertion of safety catch 5 locks screw 3 and secures the anchored medical device in clamp 2. As shown in FIG. 5, when safety catch 5 is in its final position, retention portions 11 of safety catch 5 snap in the corresponding openings 14 in clamp mechanism 2.

By pulling on tab 21, safety catch 5 can be removed due to the slightly inclined upper edge of retention portions 11. As one of ordinary skill in the art would appreciate, the reversible nature of clamping mechanism 2 may be prevented with the application of an adhesive or cement to groove 9.

Figure 7:
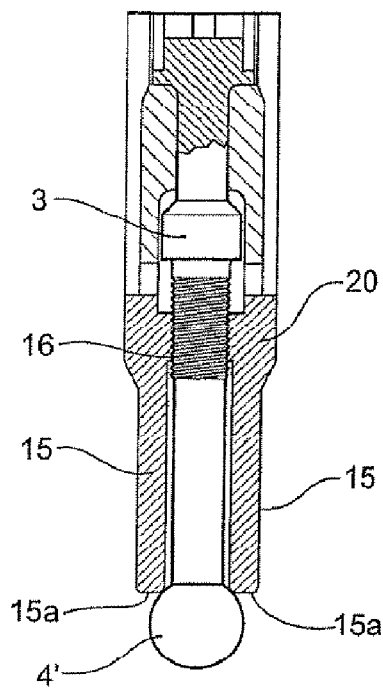
FIG. 7 is a cross-sectional view of the clamping and locking mechanism of an implantable fixation assembly according to a second embodiment of the present invention.
Figure 8:
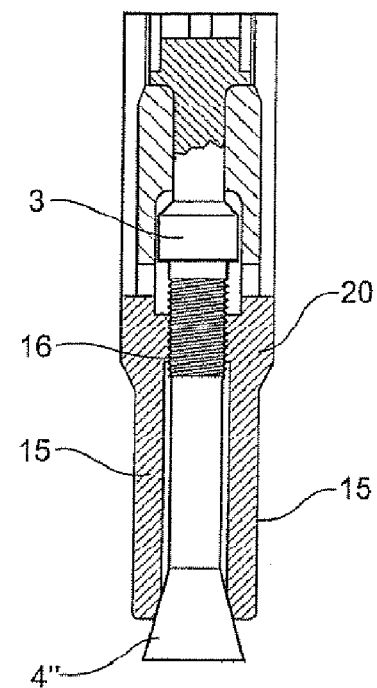
FIG. 8 is a cross-sectional view of the clamping and locking mechanism of an implantable fixation assembly according to the third embodiment of the invention.
Figure 9:
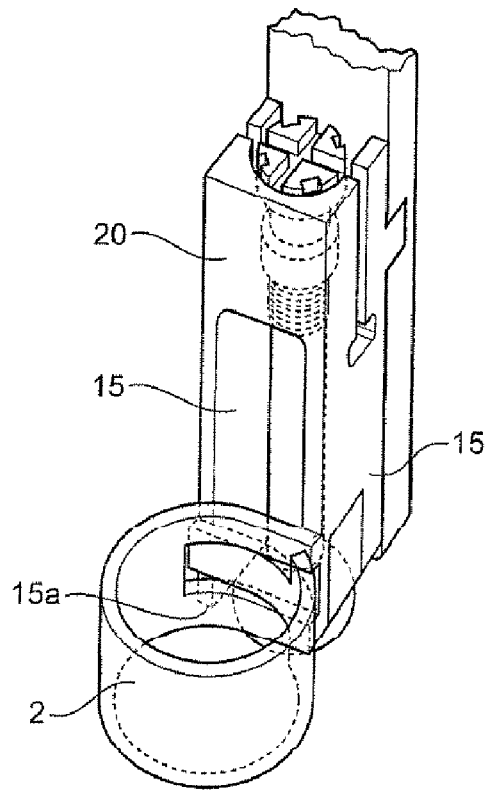
FIG. 9 is a detailed perspective view of the second embodiment of the invention.

In alternative embodiments of the invention illustrated in FIGS. 7, 8 and 9, a separate nut is not required.

Referring to FIGS. 7 and 9, components of a second embodiment of the invention will now be described. The screw 3 includes a threaded male portion 16 that mates with a female threaded portion within the body 20. At the end of the screw 3 is a bulbous portion 4' that engages the ends 15a of the legs 15. With this arrangement, as the screw 3 is tightened drawing the bulbous portion 41 inwards, the legs 15 are splayed apart causing the clamp portion 2 to close up. In this way, a medical device can be secured to the implantable fixation assembly.

Turning to FIG. 8, a third embodiment of the invention will now be described. The third embodiment of the invention is very similar to that of the second embodiment, however the bulbous portion 4' is replaced a wedge shaped portion 4". It will be appreciated that various types of screws 3 could be used other than those of the types shown in FIGS. 5a and b, 7 and 8.

Advantageously, embodiments of the implantable fixation assembly detachably anchor an implanted medical device to one or more bones of a patient. In addition, in those embodiments in which the extensions 19 and anchoring arm 18 can be bent, and extensions 19 can be severed, bone plate 1 can be modified as desired to achieve the most therapeutic position and orientation of a desired implantable medical device. Furthermore, the fixation assembly is preferably sufficiently small to permit the implantation of a medical device via a narrow incision, reducing the invasiveness of the implantation procedure. It is anticipated that only minimal manipulation of the fixation assembly will be required, further reducing the likelihood that a larger incision would be necessary.

As one of ordinary skill in the art would appreciate, the implantable fixation assembly of the present invention may be implemented with any completely- or partially-implantable medical device now or later developed. For example, embodiments of the implantable fixation assembly may be used to temporarily secure stimulators, transducers, sensors, drug-delivery devices, etc. in any location in the body, including the cranium, thorax, spinal column, etc., for any therapeutic application such as neurological, cardiac, gastrointestinal, sensory, etc. One exemplary application is to secure an embodiment of an actuator described in commonly-owned U.S. Provisional Application entitled "Implantable Actuator For Hearing Applications," U.S. application No. 60/613,512, which is hereby incorporated by reference herein in its entirety, and International Patent Application (PCT application) filed concurrently herewith entitled "IMPLANTABLE ACTUATOR FOR HEARING AID APPLICATIONS" which claims priority from said U.S. Application No. 60/613,512.

It will be understood that the term "comprise" and any of its derivatives (eg. comprises, comprising) as used in this specification and its claims is to be taken to be inclusive of features to which it refers, and is not meant to exclude the presence of any additional features unless otherwise stated or implied.

While the present invention has been described in terms of preferred embodiments in order to facilitate a better understanding of the invention, it should be appreciated that various modifications can be made without departing from the principles of the invention. Therefore, the invention should be understood to include all such modifications within the scope.

The invention claimed is:

1. An implantable fixation assembly for removably securing a medical device in a human body, the assembly comprising:
    an anchor portion having a plurality of holes, the holes facilitating attachment of the anchor portion to bone;
    a body attached to the anchor portion, the body having a pair of spaced apart legs, at least one leg being resiliently flexible, each leg having a distal end;
    a clamp portion attached towards or at the distal ends of the legs;
    a screw and nut combination having an axis of rotation longitudinal to the legs and comprising a driving member formed by said nut at an end of a shaft of the screw and which abuts an outer side of a distal end of the legs so as to produce a wedging action that induces a lateral force that pushes the legs together as the shaft is rotated so as to cause the driving member to be driven longitudinally with respect to the legs thereby actuating the clamp portion to secure the device, wherein the screw has a head, the head shaped to receive a driver, whereby a surgeon can selectively grip and release the device using the driver, movement of the driving member being reversible so as to release said lateral force and allow said legs to move apart due to the resilience of said at least one resiliently flexible leg for selectively releasing the device,
    wherein said anchor portion comprises an arm and extensions extending therefrom, and
    wherein said body is attached to the arm.

2. The assembly of claim 1, wherein the clamp portion comprises a part-cylindrical band, the band having an internal diameter that reduces as the clamp is actuated to grip the device.

3. The assembly of claim 2 wherein the band has a first end attached towards or at the distal ends of a first of the legs and a second end attached towards or at the distal ends of a second of the legs.

4. The assembly of claim 3 further comprising a safety catch, the catch operable to reversibly lock the clamp with respect to the device.

5. The assembly of claim 4 wherein the head defines a plurality of longitudinally extending slits for receiving a screw locking portion of the safety catch.

6. The assembly of claim 5 wherein the catch comprises a screw locking portion selectively engagable with the slits of the screw head.

7. The assembly of claim 6 wherein the catch further comprises flexible fingers, each finger having a retention portion that snaps into a recess within the legs or the body so as to reversibly secure the safety catch to the legs or body.

8. The assembly of claim 1, wherein the anchor portion is bendable to allow a surgeon to conform the anchor portion to a particular anatomy of a patient.

9. The assembly of claim 3 wherein the nut abuts the legs at a plane that is inclined with respect to a plane orthogonal to the axis of rotation.

10. The assembly of claim 1, wherein said arm and extensions together have a generally Y-shaped configuration.

11. The assembly of claim 1, wherein at least one of said extensions is constructed so as to be at least one of bendable and shortenable to allow a surgeon to conform the anchor portion to a particular anatomy of a patient.

12. The assembly of claim 1, wherein at least one said arm and extensions is constructed so as to be bendable to allow a surgeon to conform the anchor portion to a particular anatomy of a patient.

* * * * *